United States Patent
Hayter et al.

(10) Patent No.: US 7,653,425 B2
(45) Date of Patent: Jan. 26, 2010

(54) METHOD AND SYSTEM FOR PROVIDING CALIBRATION OF AN ANALYTE SENSOR IN AN ANALYTE MONITORING SYSTEM

(75) Inventors: Gary Hayter, Oakland, CA (US); Kenneth J. Doniger, Menlo Park, CA (US); Erwin S. Budiman, Fremont, CA (US); Songbiao Zhang, Castro Valley, CA (US); John C. Mazza, Pleasanton, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 99 days.

(21) Appl. No.: 11/463,582

(22) Filed: Aug. 9, 2006

(65) Prior Publication Data

US 2008/0039702 A1 Feb. 14, 2008

(51) Int. Cl.
- A61B 5/00 (2006.01)
- C12M 1/00 (2006.01)
- C12N 9/00 (2006.01)
- C12N 11/00 (2006.01)
- G01N 1/00 (2006.01)

(52) U.S. Cl. .................. 600/345; 600/347; 702/104; 204/403.01

(58) Field of Classification Search .................. None
See application file for complete search history.

(56) References Cited

U.S. PATENT DOCUMENTS

| | | |
|---|---|---|
| 3,581,062 A | 5/1971 | Aston |
| 3,926,760 A | 12/1975 | Allen et al. |
| 3,949,388 A | 4/1976 | Fuller |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,425,920 A | 1/1984 | Bourland et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |

(Continued)

FOREIGN PATENT DOCUMENTS

DE 4401400 7/1995

(Continued)

OTHER PUBLICATIONS

Armour, J. C., et al., "Application of Chronic Intravascular Blood Glucose Sensor in Dogs", *Diabetes*, vol. 39, 1990, pp. 1519-1526.

(Continued)

*Primary Examiner*—Robert L Nasser
(74) *Attorney, Agent, or Firm*—Jackson & Co., LLP

(57) ABSTRACT

Method and apparatus for providing calibration of analyte sensor including applying a control signal, detecting a measured response to the control signal, determining a variance in the detected measured response, and estimating a sensor sensitivity based on the variance in the detected measured response is provided.

20 Claims, 7 Drawing Sheets

U.S. PATENT DOCUMENTS

| | | |
|---|---|---|
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,854,322 A | 8/1989 | Ash et al. |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,082,550 A | 1/1992 | Rishpon et al. |
| 5,106,365 A | 4/1992 | Hernandez |
| 5,122,925 A | 6/1992 | Inpyn |
| 5,165,407 A | 11/1992 | Wilson et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,390,671 A | 2/1995 | Lord et al. |
| 5,391,250 A | 2/1995 | Cheney, II et al. |
| 5,408,999 A | 4/1995 | Singh et al. |
| 5,411,647 A | 5/1995 | Johnson et al. |
| 5,431,160 A | 7/1995 | Wilkins |
| 5,431,921 A | 7/1995 | Thombre |
| 5,462,645 A | 10/1995 | Albery et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,609,575 A | 3/1997 | Larson et al. |
| 5,628,310 A | 5/1997 | Rao et al. |
| 5,653,239 A | 8/1997 | Pompei et al. |
| 5,665,222 A | 9/1997 | Heller et al. |
| 5,711,001 A | 1/1998 | Bussan et al. |
| 5,711,861 A | 1/1998 | Ward et al. |
| 5,772,586 A | 6/1998 | Heinonen et al. |
| 5,791,344 A | 8/1998 | Schulman et al. |
| 5,899,855 A | 5/1999 | Brown |
| 5,925,021 A | 7/1999 | Castellano et al. |
| 5,942,979 A | 8/1999 | Luppino |
| 5,957,854 A | 9/1999 | Besson et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,024,699 A | 2/2000 | Surwit et al. |
| 6,049,727 A | 4/2000 | Crothall |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,233,471 B1 | 5/2001 | Berner et al. |
| 6,248,067 B1 | 6/2001 | Causey, III et al. |
| 6,275,717 B1 | 8/2001 | Gross et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,478,736 B1 | 11/2002 | Mault |
| 6,484,046 B1 | 11/2002 | Say et al. |
| 6,514,718 B2 | 2/2003 | Heller et al. |
| 6,551,494 B1 | 4/2003 | Heller et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |

| | | | | | | |
|---|---|---|---|---|---|---|
| 6,746,582 B2 | 6/2004 | Heller et al. | | 2004/0122353 A1 | 6/2004 | Shahmirian et al. |
| 6,758,810 B2 | 7/2004 | Lebel et al. | | 2004/0133164 A1 | 7/2004 | Funderburk et al. |
| 6,770,030 B1 | 8/2004 | Schaupp et al. | | 2004/0138588 A1 | 7/2004 | Saikley et al. |
| 6,790,178 B1 | 9/2004 | Mault et al. | | 2004/0152622 A1 | 8/2004 | Keith et al. |
| 6,809,653 B1 | 10/2004 | Mann et al. | | 2004/0167801 A1 | 8/2004 | Say et al. |
| 6,810,290 B2 | 10/2004 | Lebel et al. | | 2004/0171921 A1 | 9/2004 | Say et al. |
| 6,811,533 B2 | 11/2004 | Lebel et al. | | 2004/0176672 A1 | 9/2004 | Silver et al. |
| 6,811,534 B2 | 11/2004 | Bowman, IV et al. | | 2004/0186362 A1 | 9/2004 | Brauker et al. |
| 6,813,519 B2 | 11/2004 | Lebel et al. | | 2004/0186365 A1 | 9/2004 | Jin et al. |
| 6,862,465 B2 | 3/2005 | Shults et al. | | 2004/0193090 A1 | 9/2004 | Lebel et al. |
| 6,873,268 B2 | 3/2005 | Lebel et al. | | 2004/0199059 A1 | 10/2004 | Brauker et al. |
| 6,881,551 B2 | 4/2005 | Heller et al. | | 2004/0204687 A1 | 10/2004 | Mogensen et al. |
| 6,892,085 B2 | 5/2005 | McIvor et al. | | 2004/0225338 A1 | 11/2004 | Lebel et al. |
| 6,895,263 B2 | 5/2005 | Shin et al. | | 2004/0236200 A1 | 11/2004 | Say et al. |
| 6,895,265 B2 | 5/2005 | Silver | | 2004/0254433 A1 | 12/2004 | Bandis et al. |
| 6,931,327 B2 | 8/2005 | Goode, Jr. et al. | | 2004/0267300 A1 | 12/2004 | Mace |
| 6,932,894 B2 | 8/2005 | Mao et al. | | 2005/0004494 A1 | 1/2005 | Perez et al. |
| 6,936,006 B2 | 8/2005 | Sabra | | 2005/0010269 A1 | 1/2005 | Lebel et al. |
| 6,950,708 B2 | 9/2005 | Bowman, IV et al. | | 2005/0027177 A1 | 2/2005 | Shin et al. |
| 6,958,705 B2 | 10/2005 | Lebel et al. | | 2005/0031689 A1 | 2/2005 | Shults et al. |
| 6,968,294 B2 | 11/2005 | Gutta et al. | | 2005/0043598 A1 | 2/2005 | Goode, Jr. et al. |
| 6,971,274 B2 | 12/2005 | Olin | | 2005/0090607 A1 | 4/2005 | Tapsak et al. |
| 6,974,437 B2 | 12/2005 | Lebel et al. | | 2005/0112169 A1 | 5/2005 | Brauker et al. |
| 6,990,366 B2 | 1/2006 | Say et al. | | 2005/0114068 A1 | 5/2005 | Chey et al. |
| 6,997,907 B2 | 2/2006 | Safabash et al. | | 2005/0121322 A1 | 6/2005 | Say et al. |
| 6,998,247 B2 | 2/2006 | Monfre et al. | | 2005/0131346 A1 | 6/2005 | Douglas |
| 7,003,336 B2 | 2/2006 | Holker et al. | | 2005/0143635 A1 | 6/2005 | Kamath et al. |
| 7,003,340 B2 | 2/2006 | Say et al. | | 2005/0176136 A1 | 8/2005 | Burd et al. |
| 7,003,341 B2 | 2/2006 | Say et al. | | 2005/0182306 A1 | 8/2005 | Sloan |
| 7,024,245 B2 | 4/2006 | Lebel et al. | | 2005/0187720 A1 | 8/2005 | Goode, Jr. et al. |
| 7,041,068 B2 | 5/2006 | Freeman et al. | | 2005/0192557 A1 | 9/2005 | Brauker et al. |
| 7,052,483 B2 | 5/2006 | Wojcik | | 2005/0195930 A1 | 9/2005 | Spital et al. |
| 7,056,302 B2 | 6/2006 | Douglas | | 2005/0199494 A1 | 9/2005 | Say et al. |
| 7,074,307 B2 | 7/2006 | Simpson et al. | | 2005/0203360 A1 | 9/2005 | Brauker et al. |
| 7,081,195 B2 | 7/2006 | Simpson et al. | | 2005/0239154 A1* | 10/2005 | Feldman et al. ................ 435/14 |
| 7,098,803 B2 | 8/2006 | Mann et al. | | 2005/0241957 A1 | 11/2005 | Mao et al. |
| 7,108,778 B2 | 9/2006 | Simpson et al. | | 2005/0245795 A1 | 11/2005 | Goode, Jr. et al. |
| 7,110,803 B2 | 9/2006 | Shults et al. | | 2005/0245799 A1 | 11/2005 | Brauker et al. |
| 7,113,821 B1 | 9/2006 | Sun et al. | | 2005/0287620 A1 | 12/2005 | Heller et al. |
| 7,134,999 B2 | 11/2006 | Brauker et al. | | 2006/0001538 A1 | 1/2006 | Kraft et al. |
| 7,136,689 B2 | 11/2006 | Shults et al. | | 2006/0015020 A1 | 1/2006 | Neale et al. |
| 7,171,274 B2 | 1/2007 | Starkweather et al. | | 2006/0015024 A1 | 1/2006 | Brister et al. |
| 7,190,988 B2 | 3/2007 | Say et al. | | 2006/0016700 A1 | 1/2006 | Brister et al. |
| 7,192,450 B2 | 3/2007 | Brauker et al. | | 2006/0019327 A1 | 1/2006 | Brister et al. |
| 7,198,606 B2 | 4/2007 | Boecker et al. | | 2006/0020186 A1 | 1/2006 | Brister et al. |
| 7,226,978 B2 | 6/2007 | Tapsak et al. | | 2006/0020187 A1 | 1/2006 | Brister et al. |
| 7,276,029 B2 | 10/2007 | Goode, Jr. et al. | | 2006/0020188 A1 | 1/2006 | Kamath et al. |
| 7,299,082 B2 | 11/2007 | Feldman et al. | | 2006/0020189 A1 | 1/2006 | Brister et al. |
| 7,310,544 B2 | 12/2007 | Brister et al. | | 2006/0020190 A1 | 1/2006 | Kamath et al. |
| 7,335,294 B2 | 2/2008 | Heller et al. | | 2006/0020191 A1 | 1/2006 | Brister et al. |
| 2002/0019022 A1 | 2/2002 | Dunn et al. | | 2006/0020192 A1 | 1/2006 | Brister et al. |
| 2002/0042090 A1 | 4/2002 | Heller et al. | | 2006/0036139 A1 | 2/2006 | Brister et al. |
| 2002/0103499 A1 | 8/2002 | Perez et al. | | 2006/0036140 A1 | 2/2006 | Brister et al. |
| 2002/0106709 A1 | 8/2002 | Potts et al. | | 2006/0036141 A1 | 2/2006 | Kamath et al. |
| 2002/0128594 A1 | 9/2002 | Das et al. | | 2006/0036142 A1 | 2/2006 | Brister et al. |
| 2002/0161288 A1 | 10/2002 | Shin et al. | | 2006/0036143 A1 | 2/2006 | Brister et al. |
| 2003/0023317 A1 | 1/2003 | Brauker et al. | | 2006/0036144 A1 | 2/2006 | Brister et al. |
| 2003/0032874 A1 | 2/2003 | Rhodes et al. | | 2006/0036145 A1 | 2/2006 | Brister et al. |
| 2003/0042137 A1 | 3/2003 | Mao et al. | | 2006/0155180 A1* | 7/2006 | Brister et al. ................ 600/365 |
| 2003/0065308 A1 | 4/2003 | Lebel et al. | | 2006/0166629 A1 | 7/2006 | Reggiardo |
| 2003/0134347 A1 | 7/2003 | Heller et al. | | 2006/0173444 A1 | 8/2006 | Choy et al. |
| 2003/0168338 A1 | 9/2003 | Gao et al. | | 2006/0183985 A1 | 8/2006 | Brister et al. |
| 2003/0176933 A1 | 9/2003 | Lebel et al. | | 2006/0189863 A1 | 8/2006 | Heller et al. |
| 2003/0187338 A1 | 10/2003 | Say et al. | | 2006/0222566 A1 | 10/2006 | Brauker et al. |
| 2003/0199790 A1 | 10/2003 | Boecker et al. | | 2006/0229512 A1 | 10/2006 | Petisce et al. |
| 2003/0212379 A1 | 11/2003 | Bylund et al. | | 2006/0247508 A1 | 11/2006 | Fennell |
| 2003/0217966 A1 | 11/2003 | Tapsak et al. | | 2007/0027381 A1 | 2/2007 | Stafford |
| 2004/0010207 A1 | 1/2004 | Flaherty et al. | | 2007/0060814 A1 | 3/2007 | Stafford |
| 2004/0011671 A1 | 1/2004 | Shults et al. | | 2007/0073129 A1 | 3/2007 | Shah et al. |
| 2004/0040840 A1 | 3/2004 | Mao et al. | | 2007/0078320 A1 | 4/2007 | Stafford |
| 2004/0045879 A1 | 3/2004 | Shults et al. | | 2007/0078321 A1 | 4/2007 | Mazza et al. |
| 2004/0064068 A1 | 4/2004 | DeNuzzio et al. | | 2007/0078322 A1 | 4/2007 | Stafford |
| 2004/0106858 A1 | 6/2004 | Say et al. | | 2007/0106135 A1 | 5/2007 | Sloan et al. |

| | | | |
|---|---|---|---|
| 2007/0149875 A1 | 6/2007 | Ouyang et al. | |
| 2007/0163880 A1 | 7/2007 | Woo et al. | |
| 2007/0173706 A1 | 7/2007 | Neinast et al. | |
| 2007/0191701 A1 | 8/2007 | Feldman et al. | |
| 2007/0203407 A1 | 8/2007 | Hoss et al. | |
| 2007/0203966 A1 | 8/2007 | Brauker et al. | |
| 2007/0235331 A1 | 10/2007 | Simpson et al. | |
| 2007/0249922 A1 | 10/2007 | Peyser et al. | |
| 2008/0009692 A1 | 1/2008 | Stafford | |
| 2008/0017522 A1 | 1/2008 | Heller et al. | |
| 2008/0021666 A1 | 1/2008 | Goode, Jr. et al. | |
| 2008/0029391 A1 | 2/2008 | Mao et al. | |
| 2008/0081977 A1 | 4/2008 | Hayter et al. | |

FOREIGN PATENT DOCUMENTS

| | | |
|---|---|---|
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| WO | WO-96/25089 | 8/1996 |
| WO | WO-96/35370 | 11/1996 |
| WO | WO-98/35053 | 8/1998 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/076893 | 9/2003 |
| WO | WO-03/082091 | 10/2003 |
| WO | WO-03/085372 | 10/2003 |
| WO | WO-2004/061420 | 7/2004 |
| WO | WO-2005/041766 | 5/2005 |
| WO | WO-2005/089103 | 9/2005 |
| WO | WO-2006/024671 | 3/2006 |
| WO | WO-2006/079114 | 7/2006 |
| WO | WO-2006/118947 | 11/2006 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |

OTHER PUBLICATIONS

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet.*

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain The Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems, Chapter 15*, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring, Chapter 4*, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

International Preliminary Report on Patentability and Written Opinion of the International Searching Authority for PCT Application No. PCT/US2007/075522 filed Aug. 8, 2007, mailed Feb. 19, 2009.

International Search Report and Written Opinion of the International Searching Authority for PCT Application No. PCT/US2007/075522 filed Aug. 8, 2007 to Abbott Diabetes Care, Inc., mailed Sep. 24, 2008.

* cited by examiner

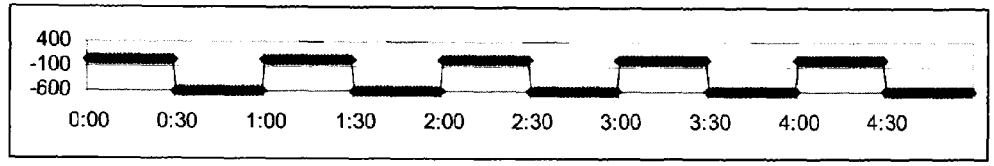
FIGURE 7A
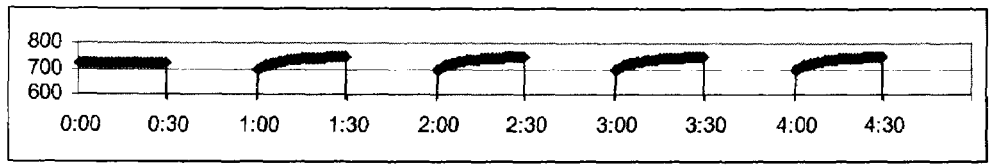
FIGURE 7B
| | Measurement Response Difference (ADC counts) | Sensor Sensitivity pA/(mg/dL) |
|---|---|---|
| | .... | |
| | 43 | 33.7 |
| | 44 | 33.9 |
| | 45 | 34.1 |
| | 46 | 34.3 |
| → | 47 | 34.5 |
| | 48 | 34.7 |
| | 49 | 34.9 |
| | 50 | 35.1 |
| | 51 | 35.3 |
| | | .... |
FIGURE 8

METHOD AND SYSTEM FOR PROVIDING CALIBRATION OF AN ANALYTE SENSOR IN AN ANALYTE MONITORING SYSTEM

BACKGROUND

Analyte, e.g., glucose monitoring systems including continuous and discrete monitoring systems generally include a small, lightweight battery powered and microprocessor controlled system which is configured to detect signals proportional to the corresponding measured glucose levels using an electrometer, and RF signals to transmit the collected data. One aspect of certain analyte monitoring systems include a transcutaneous or subcutaneous analyte sensor configuration which is, for example, partially mounted on the skin of a subject whose analyte level is to be monitored. The sensor cell may use a two or three-electrode (work, reference and counter electrodes) configuration driven by a controlled potential (potentiostat) analog circuit connected through a contact system.

To obtain accurate data from the analyte sensor, calibration is necessary. Typically, blood glucose measurements are periodically obtained using, for example, a blood glucose meter, and the measured blood glucose values are used to calibrate the sensors. Indeed, the patient must calibrate each new analyte sensor using for example, capillary blood glucose measurements. This may be inconvenient for the patient.

In view of the foregoing, it would be desirable to have a method and system for calibrating analyte sensors of an analyte monitoring system that does not inconveniently require periodic blood glucose measurements for sensor calibration.

SUMMARY OF THE INVENTION

In view of the foregoing, in accordance with the various embodiments of the present invention, there is provided a method and system for providing substantially automatic and substantially real time calibration of analyte sensors for use in an analyte monitoring system.

These and other objects, features and advantages of the present invention will become more fully apparent from the following detailed description of the embodiments, the appended claims and the accompanying drawings.

BRIEF DESCRIPTION OF THE DRAWINGS

FIG. 7A illustrates the transmission of the control signal from the transmitter processor in accordance with one embodiment of the present invention;

FIG. 7B illustrates the measured response to the control signal from the transmitter processor shown in FIG. 7A in accordance with one embodiment of the present invention;

FIG. 8 is a tabular illustration of a lookup table for sensor sensitivity for use with the calibration procedure in accordance with one embodiment of the present invention.

DETAILED DESCRIPTION

As described in detail below, in accordance with the various embodiments of the present invention, there is provided a method and system for determining sensor sensitivity of an analyte sensor which may be used to calibrate the analyte sensor in the analyte monitoring system. In particular, within the scope of the present invention, there is provided method and system for automatically calibrating subcutaneous or transcutaneously positioned analyte sensors such that the frequency of capillary blood glucose measurement for calibration of the sensors may be minimized.

Figure 1:
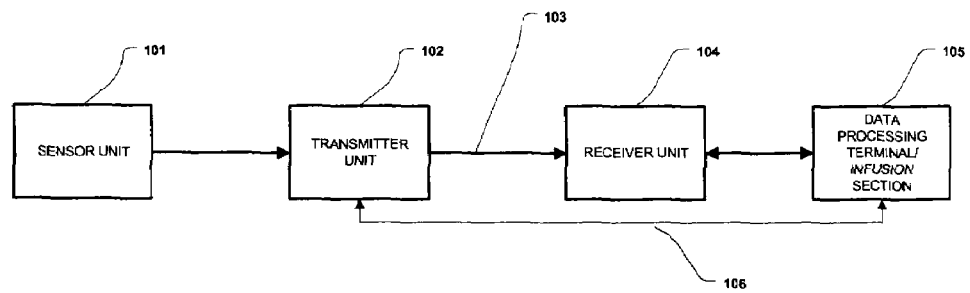
FIG. 1 illustrates a block diagram of a data monitoring and management system for practicing one embodiment of the present invention.

More specifically, FIG. 1 illustrates a data monitoring and management system such as, for example, analyte (e.g., glucose) monitoring system 100 in accordance with one embodiment of the present invention. The subject invention is further described primarily with respect to a glucose monitoring system for convenience and such description is in no way intended to limit the scope of the invention. It is to be understood that the analyte monitoring system may be configured to monitor a variety of analytes, e.g., lactate, and the like.

Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored.

The analyte monitoring system 100 includes a sensor 101, a transmitter unit 102 coupled to the sensor 101, and a receiver unit 104 which is configured to communicate with the transmitter unit 102 via a communication link 103. The receiver unit 104 may be further configured to transmit data to a data processing terminal 105 for evaluating the data received by the receiver unit 104. Moreover, the data processing terminal in one embodiment may be configured to receive data directly from the transmitter unit 102 via a communication link 106 which may optionally be configured for bi-directional communication.

Only one sensor 101, transmitter unit 102, receiver unit 104, communication link 103, and data processing terminal 105 are shown in the embodiment of the analyte monitoring system 100 illustrated in FIG. 1. However, it will be appreciated by one of ordinary skill in the art that the analyte monitoring system 100 may include one or more sensor 101, transmitter unit 102, receiver unit 104, communication link 103, and data processing terminal 105. Moreover, within the scope of the present invention, the analyte monitoring system 100 may be a continuous monitoring system, or semi-continuous, or a discrete monitoring system. In a multi-component environment, each device is configured to be uniquely identified by each of the other devices in the system so that communication conflict is readily resolved between the various components within the analyte monitoring system 100.

In one embodiment of the present invention, the sensor 101 is physically positioned in or on the body of a user whose analyte level is being monitored. The sensor 101 may be configured to continuously sample the analyte level of the user and convert the sampled analyte level into a corresponding data signal for transmission by the transmitter unit 102. In one embodiment, the transmitter unit 102 is mounted on the sensor 101 so that both devices are positioned on the user's body. The transmitter unit 102 performs data processing such as filtering and encoding on data signals, each of which corresponds to a sampled analyte level of the user, for transmission to the receiver unit 104 via the communication link 103.

In one embodiment, the analyte monitoring system 100 is configured as a one-way RF communication path from the transmitter unit 102 to the receiver unit 104. In such embodiment, the transmitter unit 102 transmits the sampled data signals received from the sensor 101 without acknowledgement from the receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the receiver unit 104 may be configured to detect such transmitted encoded sampled data signals at predetermined time intervals. Alternatively, the analyte monitoring system 100 may be configured with a bi-directional RF (or otherwise) communication between the transmitter unit 102 and the receiver unit 104.

Additionally, in one aspect, the receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the receiver unit 104 is a data processing section which is configured to process the data signals received from the transmitter unit 102 such as by performing data decoding, error detection and correction, data clock generation, and data bit recovery.

In operation, upon completing the power-on procedure, the receiver unit 104 is configured to detect the presence of the transmitter unit 102 within its range based on, for example, the strength of the detected data signals received from the transmitter unit 102 or a predetermined transmitter identification information. Upon successful synchronization with the corresponding transmitter unit 102, the receiver unit 104 is configured to begin receiving from the transmitter unit 102 data signals corresponding to the user's detected analyte level. More specifically, the receiver unit 104 in one embodiment is configured to perform synchronized time hopping with the corresponding synchronized transmitter unit 102 via the communication link 103 to obtain the user's detected analyte level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected analyte level of the user.

Within the scope of the present invention, the data processing terminal 105 may include an infusion device such as an insulin infusion pump or the like, which may be configured to administer insulin to patients, and which may be configured to communicate with the receiver unit 104 for receiving, among others, the measured analyte level. Alternatively, the receiver unit 104 may be configured to integrate an infusion device therein so that the receiver unit 104 is configured to administer insulin therapy to patients, for example, for administering and modifying basal profiles, as well as for determining appropriate boluses for administration based on, among others, the detected analyte levels received from the transmitter unit 102.

Additionally, the transmitter unit 102, the receiver unit 104 and the data processing terminal 105 may each be configured for bi-directional wireless communication such that each of the transmitter unit 102, the receiver unit 104 and the data processing terminal 105 may be configured to communicate (that is, transmit data to and receive data from) with each other via the wireless communication link 103. More specifically, the data processing terminal 105 may in one embodiment be configured to receive data directly from the transmitter unit 102 via the communication link 106, where the communication link 106, as described above, may be configured for bi-directional communication.

In this embodiment, the data processing terminal 105 which may include an insulin pump, may be configured to receive the analyte signals from the transmitter unit 102, and thus, incorporate the functions of the receiver 103 including data processing for managing the patient's insulin therapy and analyte monitoring. In one embodiment, the communication link 103 may include one or more of an RF communication protocol, an infrared communication protocol, a Bluetooth enabled communication protocol, an 802.11x wireless communication protocol, or an equivalent wireless communication protocol which would allow secure, wireless communication of several units (for example, per HIPPA requirements) while avoiding potential data collision and interference.

Figure 2:
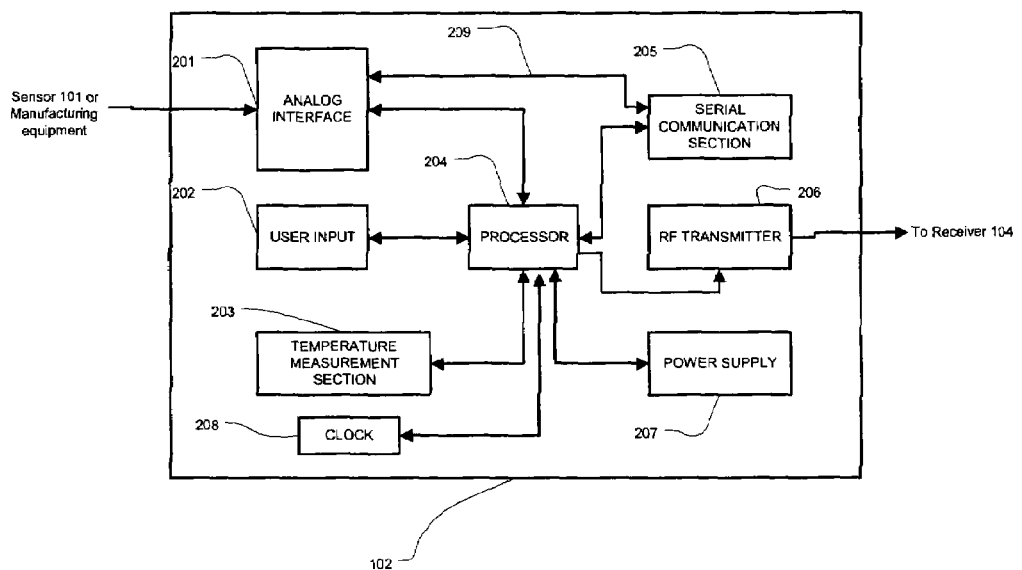
FIG. 2 is a block diagram of the transmitter unit of the data monitoring and management system shown in FIG. 1 in accordance with one embodiment of the present invention.

FIG. 2 is a block diagram of the transmitter of the data monitoring and detection system shown in FIG. 1 in accordance with one embodiment of the present invention. Referring to the Figure, the transmitter unit 102 in one embodiment includes an analog interface 201 configured to communicate with the sensor 101 (FIG. 1), a user input 202, and a temperature detection section 203, each of which is operatively coupled to a transmitter processor 204 such as a central processing unit (CPU). As can be seen from FIG. 2, there are provided four contacts, three of which are electrodes—work electrode, guard contact, reference electrode, and counter electrode, each operatively coupled to the analog interface 201 of the transmitter unit 102 for connection to the sensor unit 201 (FIG. 1). In one embodiment, each of the work electrode, guard contact, reference electrode, and counter electrode may be made using a conductive material that is either printed or etched, for example, such as carbon which may be printed, or metal foil (e.g., gold) which may be etched.

Further shown in FIG. 2 are a transmitter serial communication section 205 and an RF transmitter 206, each of which is also operatively coupled to the transmitter processor 204. Moreover, a power supply 207 such as a battery is also provided in the transmitter unit 102 to provide the necessary power for the transmitter unit 102. Additionally, as can be seen from the Figure, clock 208 is provided to, among others, supply real time information to the transmitter processor 204.

In one embodiment, a unidirectional input path is established from the sensor 101 (FIG. 1) and/or manufacturing and testing equipment to the analog interface 201 of the transmitter unit 102, while a unidirectional output is established from the output of the RF transmitter 206 of the transmitter unit 102 for transmission to the receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter unit 102 is configured to transmit to the receiver unit 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter unit 102 for operation upon completion of the manufacturing process as well as for direct communication for diagnostic and testing purposes.

As discussed above, the transmitter processor 204 is configured to transmit control signals to the various sections of the transmitter unit 102 during the operation of the transmitter unit 102. In one embodiment, the transmitter processor 204 also includes a memory (not shown) for storing data such as the identification information for the transmitter unit 102, as well as the data signals received from the sensor 101. The stored information may be retrieved and processed for transmission to the receiver unit 104 under the control of the transmitter processor 204. Furthermore, the power supply 207 may include a commercially available battery.

The transmitter unit 102 is also configured such that the power supply section 207 is capable of providing power to the transmitter for a minimum of about three months of continuous operation after having been stored for about eighteen months in a low-power (non-operating) mode. In one embodiment, this may be achieved by the transmitter processor 204 operating in low power modes in the non-operating state, for example, drawing no more than approximately 1 µA of current. Indeed, in one embodiment, the final step during the manufacturing process of the transmitter unit 102 may place the transmitter unit 102 in the lower power, non-operating state (i.e., post-manufacture sleep mode). In this manner, the shelf life of the transmitter unit 102 may be significantly improved.

Moreover, as shown in FIG. 2, while the power supply unit 207 is shown as coupled to the processor 204, and as such, the processor 204 is configured to provide control of the power supply unit 207, it should be noted that within the scope of the present invention, the power supply unit 207 is configured to provide the necessary power to each of the components of the transmitter unit 102 shown in FIG. 2.

Referring back to FIG. 2, the power supply section 207 of the transmitter unit 102 in one embodiment may include a rechargeable battery unit that may be recharged by a separate power supply recharging unit (for example, provided in the receiver unit 104) so that the transmitter unit 102 may be powered for a longer period of usage time. Moreover, in one embodiment, the transmitter unit 102 may be configured without a battery in the power supply section 207, in which case the transmitter unit 102 may be configured to receive power from an external power supply source (for example, a battery) as discussed in further detail below.

Referring yet again to FIG. 2, the temperature detection section 203 of the transmitter unit 102 is configured to monitor the temperature of the skin near the sensor insertion site. The temperature reading is used to adjust the analyte readings obtained from the analog interface 201. The RF transmitter 206 of the transmitter unit 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the receiver unit 104.

Additional detailed description of the continuous analyte monitoring system, its various components including the functional descriptions of the transmitter are provided in U.S. Pat. No. 6,175,752 issued Jan. 16, 2001 entitled "Analyte Monitoring Device and Methods of Use", and in application Ser. No. 10/745,878 filed Dec. 26, 2003 entitled "Continuous Glucose Monitoring System and Methods of Use", each assigned to the Assignee of the present application.

Figure 3:
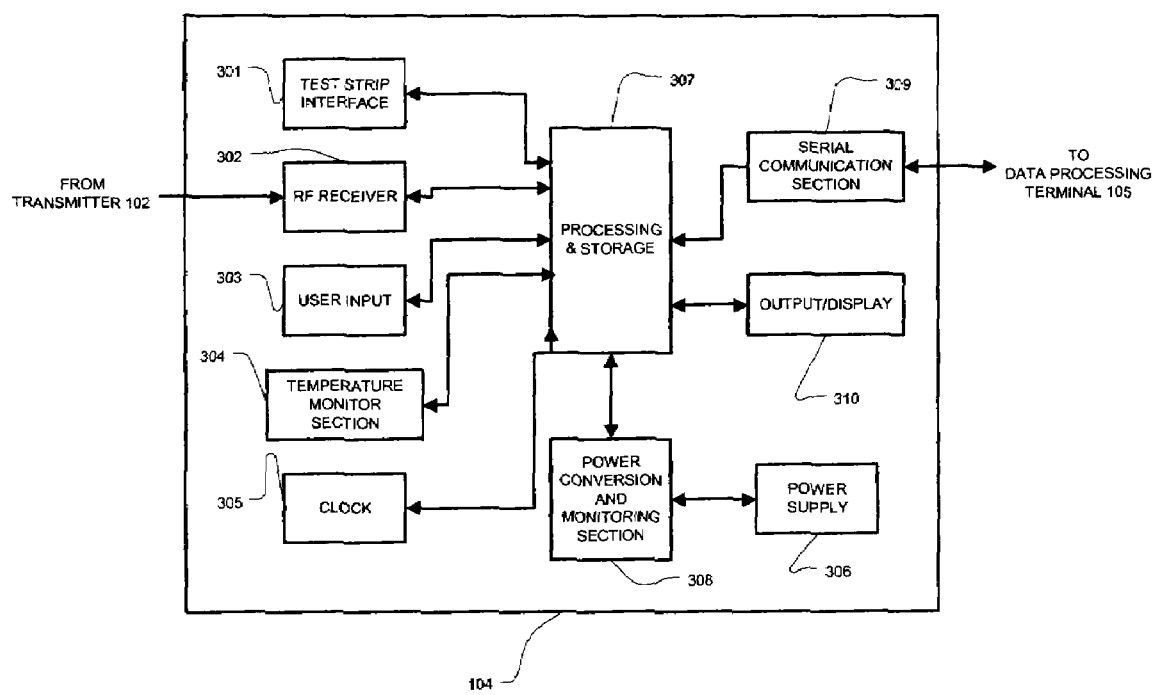
FIG. 3 is a block diagram of the receiver/monitor unit of the data monitoring and management system shown in FIG. 1 in accordance with one embodiment of the present invention.

FIG. 3 is a block diagram of the receiver/monitor unit of the data monitoring and management system shown in FIG. 1 in accordance with one embodiment of the present invention. Referring to FIG. 3, the receiver unit 104 includes a blood glucose test strip interface 301, an RF receiver 302, an input 303, a temperature detection section 304, and a clock 305, each of which is operatively coupled to a receiver processor 307. As can be further seen from the Figure, the receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the receiver processor 307.

In one embodiment, the test strip interface 301 includes a glucose level testing portion to receive a manual insertion of a glucose test strip, and thereby determine and display the glucose level of the test strip on the output 310 of the receiver unit 104. This manual testing of glucose can be used to calibrate sensor 101. The RF receiver 302 is configured to communicate, via the communication link 103 (FIG. 1) with the RF transmitter 206 of the transmitter unit 102, to receive encoded data signals from the transmitter unit 102 for, among others, signal mixing, demodulation, and other data processing. The input 303 of the receiver unit 104 is configured to allow the user to enter information into the receiver unit 104 as needed. In one aspect, the input 303 may include one or more keys of a keypad, a touch-sensitive screen, or a voice-activated input command unit. The temperature detection section 304 is configured to provide temperature information of the receiver unit 104 to the receiver processor 307, while the clock 305 provides, among others, real time information to the receiver processor 307.

Each of the various components of the receiver unit 104 shown in FIG. 3 is powered by the power supply 306 which, in one embodiment, includes a battery. Furthermore, the power conversion and monitoring section 308 is configured to monitor the power usage by the various components in the receiver unit 104 for effective power management and to alert the user, for example, in the event of power usage which renders the receiver unit 104 in sub-optimal operating conditions. An example of such sub-optimal operating condition may include, for example, operating the vibration output mode (as discussed below) for a period of time thus substantially draining the power supply 306 while the processor 307 (thus, the receiver unit 104) is turned on. Moreover, the power conversion and monitoring section 308 may additionally be configured to include a reverse polarity protection circuit such as a field effect transistor (FET) configured as a battery activated switch.

The serial communication section 309 in the receiver unit 104 is configured to provide a bi-directional communication path from the testing and/or manufacturing equipment for, among others, initialization, testing, and configuration of the receiver unit 104. Serial communication section 104 can also be used to upload data to a computer, such as time-stamped blood glucose data. The communication link with an external device (not shown) can be made, for example, by cable, infrared (IR) or RF link. The output 310 of the receiver unit 104 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones presently available. In a further embodiment, the receiver unit 104 also includes an electro-luminescent lamp configured to provide backlighting to the output 310 for output visual display in dark ambient surroundings.

Referring back to FIG. 3, the receiver unit 104 in one embodiment may also include a storage section such as a programmable, non-volatile memory device as part of the processor 307, or provided separately in the receiver unit 104, operatively coupled to the processor 307. The processor 307 is further configured to perform Manchester decoding as well as error detection and correction upon the encoded data signals received from the transmitter unit 102 via the communication link 103.

Referring back to the Figures, as described in further detail below, in one embodiment of the present invention, the transmitter processor 204 may be configured to transmit a control signal to the analog interface 201 to determine the poise voltage between the work electrode and the reference electrode of the sensor unit 101, each of which are operatively coupled to the analog interface 201 of the transmitter unit 102.

More specifically, in one embodiment, a control processor component of the transmitter unit 102 processor 204 is configured to provide a perturbation control signal to the analog interface 201. The analog interface 201 is configured to translate the received perturbation control signal to a perturbation that affects the sensor response. For example, the control signal in one embodiment may be configured to control the voltage level that is applied to the sensor 101 between the work and reference electrodes (i.e., the poise voltage). In one embodiment, the analog interface 201 of the transmitter unit 102 is configured to translate the sensor response to the perturbation to a corresponding response signal that is acquired by the signal processing component of the processor 204 of the transmitter unit 102. The signal processing component of the processor 204 in the transmitter unit 102 in one embodiment may be configured to determine the desired sensor parameter estimation which is transmitted to the receiver unit 104. Alternatively, the signal processing component of the processor 204 in the transmitter unit 102 may be configured to preprocess the data, which are then transmitted to the receiver unit for sensor parameter estimation determination.

Figure 4:
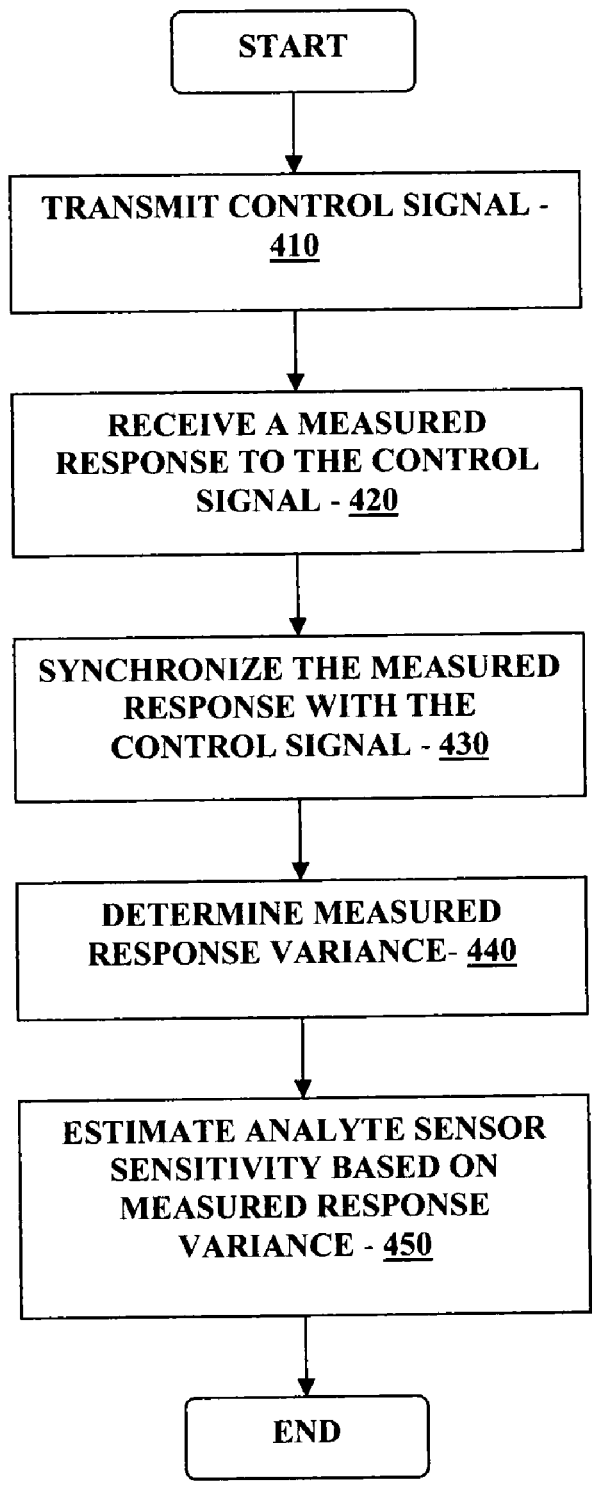
FIG. 4 is a flowchart illustrating analyte sensor sensitivity estimation procedure in accordance with one embodiment of the present invention.

More specifically, FIG. 4 is a flowchart illustrating analyte sensor sensitivity estimation procedure in accordance with one embodiment of the present invention. Referring to FIG. 4, at step 410, the transmitter processor 204 (FIG. 2) in one embodiment is configured to provide a control signal to the analog interface 201 (for example a poise voltage control circuit) of the transmitter unit 102. In one aspect, the control signal provides a perturbation input to determine the poise voltage between the work electrode and the reference electrode of the sensor unit 101. In one aspect, the poise voltage may be in the range of approximately −600 mV and 600 mV, and the analog interface 201 may be configured to control the poise voltage and apply the poise voltage to the electrodes of the sensor unit 101.

One embodiment of the control signal perturbations is shown in FIG. 7A which illustrates the control signal from the transmitter processor 204 so as to provide a poise voltage waveform that is a square wave of 50% duty cycle with a one minute time period interval. In one embodiment, the poise voltage square wave amplitude may be switched from 40 mV to −600 mV from, for example, the normal operating poise voltage to a predetermined level such as −600 mV which effectively shuts down the current signal on the work electrode.

Referring back to FIG. 4, at step 420, the analog interface 201 in one embodiment is configured to determine a measured response to the received control signal, for example, a voltage signal which is substantially proportional to the current signal level on the work electrode of the sensor unit 101. An aspect of the measured response is illustrated in FIG. 7B. As shown, in one aspect, the current signal level is associated with the analyte level of the patient and may be modulated by the poise voltage perturbations driven by the control signal from the transmitter processor 204. Thereafter at step 430, the transmitter processor 204 may be optionally configured to synchronize the measured response from the analog interface 201 with the control signal. The transmitter processor 204 may be further configured to store the measured response and the associated control signal in a storage unit (not shown) such as a memory device.

Referring again to FIG. 4, the transmitter processor 204 in one embodiment is configured to determine the difference or variance in the measured response based on the control signal, and the sensor sensitivity may be determined based on the determined difference in measured response. That is, in one embodiment, the difference in measured response is compared to a look up table stored, for example, in the transmitter processor 204 memory unit which includes calculated measured response difference for the sensor based on characteristics of the sensor unit 101.

By way of an example, for a measured response difference of 37 analog to digital counts, the lookup table for sensor sensitivity (FIG. 8) indicates 34.5 pA/(mg/dL) for the sensor. Then, the determined sensor sensitivity may be applied to the work electrode current to determine the corresponding calibrated analyte value. That is, the calibrated analyte value may be determined by dividing the work electrode current signal by the sensor sensitivity.

Figure 5:
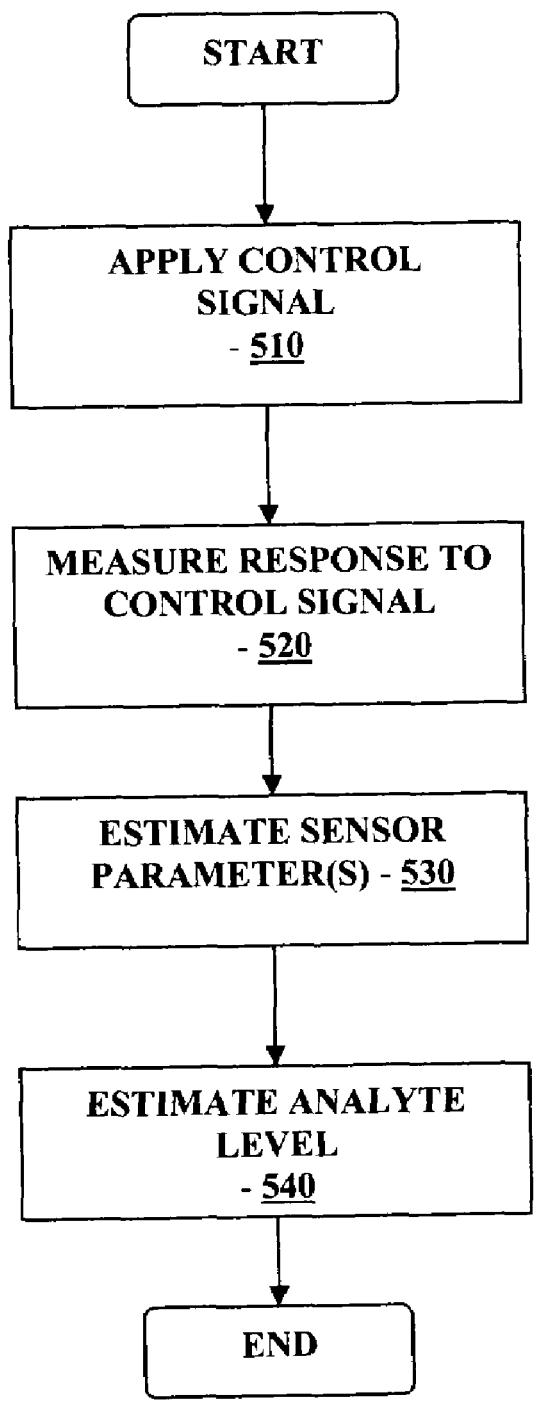
FIG. 5 is a flowchart illustrating the analyte sensor sensitivity estimation procedure in accordance with another embodiment of the present invention.

FIG. 5 is a flowchart illustrating the analyte sensor sensitivity estimation procedure in accordance with another embodiment of the present invention. Referring to FIG. 5, at step 510, a perturbation control signal is applied to the sensor 101 (FIG. 1), and then the response to the perturbation control signal is measured at step 520. Based on the measured response to the perturbation control signal, at step 530 the sensor parameter(s) is estimated and at step 540, the analyte level is estimated based on the measured response to the perturbation control signal. In one embodiment, the procedure shown in FIG. 5 is repeated continuously.

In accordance with the various embodiments of the present invention, different estimates may be determined including, for example, estimation of sensor properties such as sensitivity and response time, the analyte level, and analyte level validity/accuracy. In one embodiment, there are several mechanisms that may be used to perturb the sensor 101 (FIG. 1), for example, the variable poise voltage. In a further aspect, the one or more of the perturbation control signals may include, for example, square waves. Also, in one aspect, the one or more physical sensor responses that is measured may include, for example, work electrode current variation due to poise voltage perturbation. In addition, signal processing may be used in one embodiment to estimate the sensor parameter or analyte level from the sensor response to the perturbation as described above.

Figure 6:
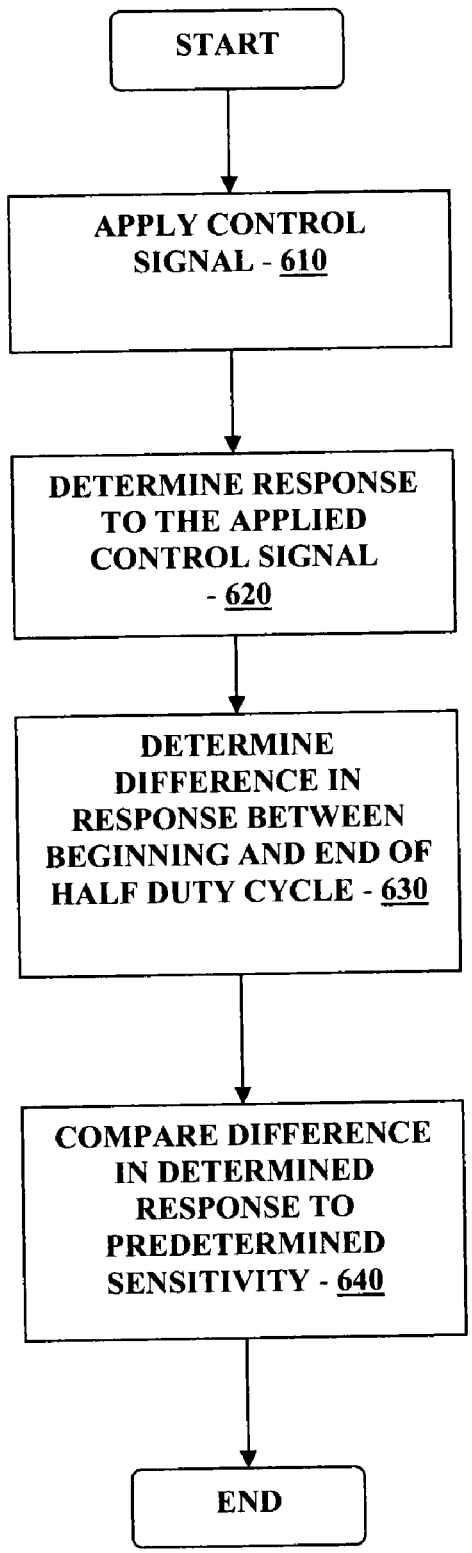
FIG. 6 is a flowchart illustrating an analyte sensor parameter estimation procedure in accordance with one embodiment of the present invention.

FIG. 6 is a flowchart illustrating an analyte sensor parameter estimation procedure in accordance with one embodiment of the present invention. Referring to FIG. 6, a control signal is applied, for example, to the analog interface 201 of the transmitter unit 102 (FIG. 1). That is, in one embodiment, the processor 204 of the transmitter unit 102 may be configured to provide a control signal to a poise voltage control circuit (for example, incorporated in the processor 204 of the transmitter unit 102 as shown in FIG. 2, but which may, in one embodiment, may be separately provided within the transmitter unit 102) of the transmitter unit 102.

In one aspect, the control signal may be configured to provide a perturbation input signal to determine the poise voltage between the work electrode and the reference electrode of the sensor unit 101. In one embodiment, the poise voltage may be in the range of approximately −600 mV and 600 mV, and the analog interface 201 may be configured to control the poise voltage and apply the poise voltage to the electrodes of the sensor unit 101.

As described in further detail below, an embodiment of the control signal perturbations is shown in FIG. 7A which illustrates the control signal from the processor 204 (FIG. 2) to provide a poise voltage waveform that is a square wave of 50% duty cycle with a one minute time period interval. Referring to FIG. 7A, in one embodiment, the poise voltage square wave amplitude may be switched from 40 mV to −600 mV from, for example, the normal operating poise voltage to a predetermined level such as −600 mV which effectively shuts down the current signal on the work electrode.

Referring back to FIG. 6, the analog interface 201 in one embodiment is configured to determine a measured response to the received control signal, for example, a voltage signal which is substantially proportional to the current signal level on the work electrode of the sensor unit 101 (FIG. 1). As discussed in further detail below, one embodiment of the measured response is shown in FIG. 7B. Referring to FIG. 7B, in one embodiment, the average signal level for half of the duty cycle is associated with the analyte level of the patient, but the transient within the half-duty cycle period, caused by the poise voltage perturbations driven by the control signal from the transmitter processor 204, is associated with the sensitivity parameter of the sensor 101. The transmitter processor 204 may be further configured to store the measured response and the associated control signal in a storage unit (not shown) such as a memory device.

Referring again to FIG. 6, the transmitter processor 204 in one embodiment is configured to determine the amplitude difference of the transient from the start of the half-duty cycle to the end (referred to sometimes as the "on" period) in the measured response, and the sensor sensitivity may be determined based on the determined difference in the response. That is, in one embodiment, the difference in measured response is compared to a predetermined sensor parameter such as sensor sensitivity that may be stored in a look up table, for example, in the transmitter processor 204 memory unit. In one aspect, the look up table may include a calculated measured response difference for the sensor unit 101 and corresponding sensor sensitivities based on characteristics of the sensor unit 101.

By way of an example, for a measured response difference of 47 analog to digital counts, the lookup table for sensor sensitivity as shown in FIG. 8 indicates 34.5 pA/(mg/dL) for the sensor. In one embodiment, the transmitter may be configured to determine this sensitivity value once per minute, and to transmit the sensitivity value it to the receiver unit 104 (FIG. 1) in addition to data or signal corresponding to the work current signal level, determined at the end of the "on" period, and skin temperature.

In one embodiment, the receiver unit 104 (FIG. 1) may be configured to apply the determined sensor sensitivity to the temperature compensated work electrode current signal in order to determine the corresponding calibrated analyte value or level. That is, the calibrated analyte value may be determined by dividing the temperature compensated work electrode current signal by the determined sensor sensitivity. In one aspect, a time-series of the calibrated analyte values may be acquired by the receiver unit 104 (FIG. 1) in real-time, and may be used to determine analyte rate-of-change and other analyte signal metrics and/or statistics. In addition, the calibrated analyte values may also be used to drive alarms or alerts that inform the patient whose analyte is being monitored of analyte level conditions that require attention. In addition, in accordance with one aspect of the present invention, the receiver unit 104 may be configured to determine whether the sensor sensitivity range is within a valid range.

FIG. 7A illustrates the transmission of the control signal from the transmitter processor in accordance with one embodiment of the present invention. More particularly, FIG. 7A illustrates the poise voltage square wave with 50% duty cycle with one minute time periods is shown, where the poise voltage square wave amplitude is switched from 40 mV to −600 mV as in normal operating mode. FIG. 7B illustrates the measured response to the control signal from the transmitter processor shown in FIG. 7A in accordance with one embodiment of the present invention. More specifically, the measured response which is associated with the analyte level measured by the sensor unit 101 from the interstitial fluid of a patient as modulated by the control signal from the transmitter processor 204 is illustrated with one minute time periods FIG. 8 is a tabular illustration of a lookup table for sensor sensitivity for use with the calibration procedure in accordance with one embodiment of the present invention. More specifically, in one embodiment, the lookup table shown in FIG. 8 is stored in a memory unit (not shown) of the transmitter unit 102 (or alternatively, in the transmitter processor 204) and may be accessed by the transmitter processor 204 to retrieve a corresponding sensitivity value associated with the determined measured response difference.

Figure 9:
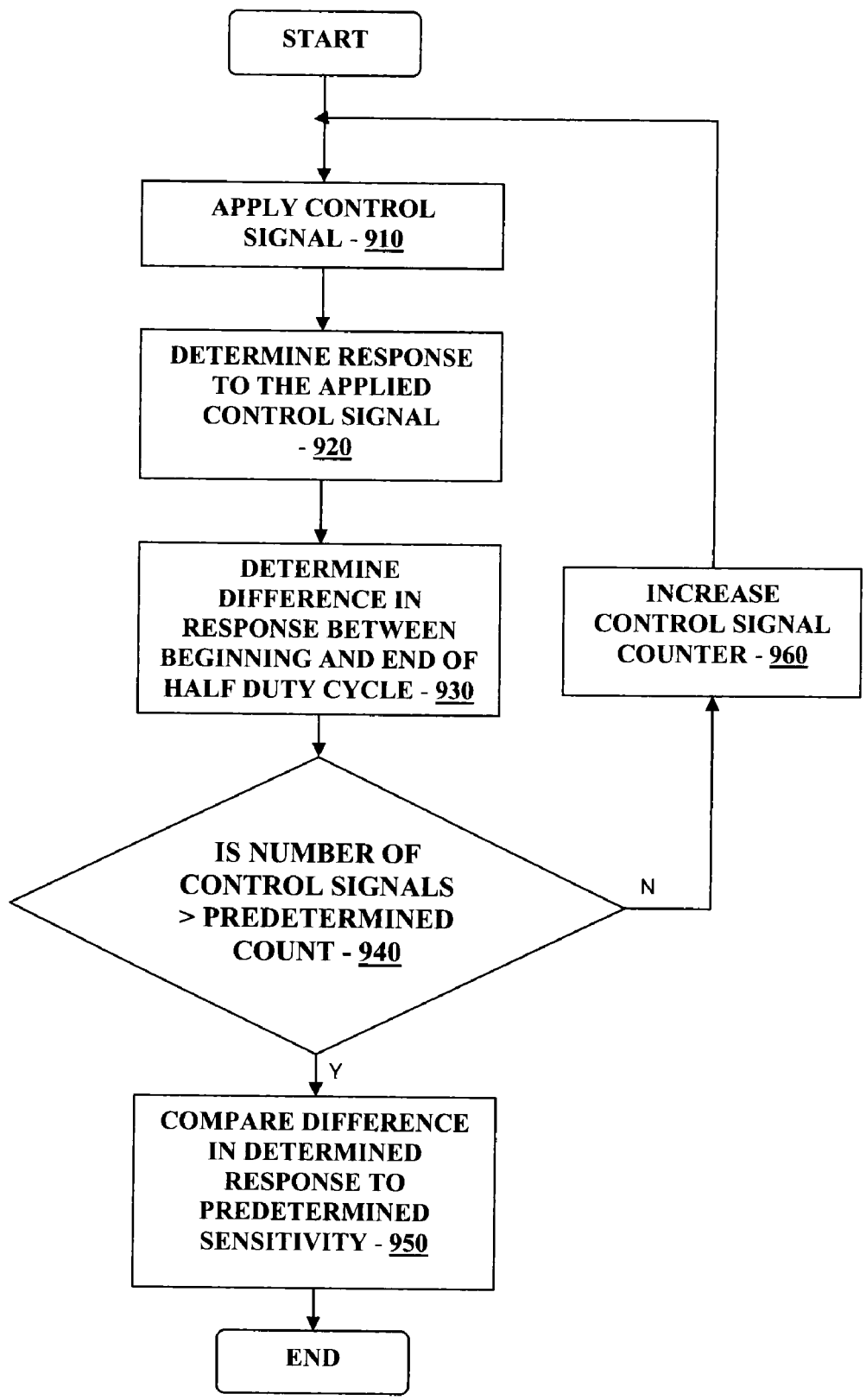
FIG. 9 is a flowchart illustrating the analyte sensor sensitivity estimation procedure in accordance with another embodiment of the present invention.

FIG. 9 is a flowchart illustrating the analyte sensor sensitivity estimation procedure in accordance with another embodiment of the present invention. Referring to FIG. 9, in one embodiment, a control signal from the transmitter processor 204 (FIG. 2) is provided to the transmitter unit 102 analog interface 201, and a response to the applied control signal is determined. Thereafter, the difference or variance in the determined response to the control signal between the beginning and end of the half duty cycle is determined. As can be seen, in one embodiment, steps 910 to 930 are substantially similar to steps 610 to 630, respectively described above.

Referring back to FIG. 9, after determining the measured response variance or difference between the beginning and end of the half duty cycle, it is determined whether the number of transmitted or applied control signals exceed a predetermined number or count. If it is determined that the number of transmitted or applied control signals do not exceed the predetermined number or count, then a control signal counter (for example, provided in the transmitter unit 102) is incremented by one count, and the routine returns to the beginning where another control signal is provided to the analog interface 201 of the transmitter unit 102.

On the other hand, if it is determined that the number of transmitted or applied control signals exceed the predetermined number or count, then the sensor sensitivity may be determined based on the determined difference in the response. That is, as discussed above, the difference in measured response in one embodiment is compared to a predetermined sensor parameter such as sensor sensitivity that may be stored in a look up table, for example, in the transmitter processor 204 memory unit. In one aspect, the look up table may include a calculated measured response difference for the sensor and corresponding sensor sensitivities based on characteristics of the sensor. Furthermore, as discussed above, in one embodiment, the calibrated analyte value or level may be determined by, for example, dividing the corresponding sensor signal (e.g., work electrode current signal) level by the determined sensor sensitivity value.

Within the scope of the present invention, the perturbations to the analyte sensors may be provided by, for example, altering the poise voltage in time. Alternatively, an additional electrical current signal may be provided to the sensor work or counter electrodes via an AC coupling, where the level of the additional electrical current signal may be varied in time by the control signal in a manner similar as discussed above. Still in accordance with another embodiment, the work/counter electrode current path may be opened and closed in a time varying manner controlled by the control signal. Yet still another embodiment may provide a variable resistance in the work/counter electrode current path, where the variable resistance is varied in time as controlled by the control signal.

In another aspect of the present invention, the transcutaneously positioned sensor may be perturbed with a mechanical transducer controlled in time and amplitude by a predetermined control signal. In one embodiment, mechanical transducers may include those that can provide physical signals of vibration, acoustics, thermal or electro-magnetic media, for example. Broadly, any suitable mechanism to apply perturbations to the transcutaneously positioned sensor may be used to the extent that the measured response may be analyzed by the signal processing component such as, for example, the transmitter unit processor 204 to estimate one or more sensor properties based on the signal response induced by the perturbations. For example, vibration perturbations may induce fluctuations in the sensor membrane that could be detected in the measured response transients, which may be correlated with membrane thickness and thus provide a measure of the sensitivity of the sensor.

In addition, in accordance with the various embodiments of the present invention, there are provided a variety of time-varying controls signals that may be applied, along with a variety of techniques used to analyze the measured response and estimate the sensor parameter of interest. Some of these control signals may be appropriate to induce a measured response that is more informative about a specific sensor parameter than other control signals, and some control signals may be more practical to implement than others. As discussed previously, a square-wave control signal may be employed in one embodiment. Variations in this type of control signal may be suitably used where the positive and negative amplitudes are at different levels, the duty cycle is other than 50%, or the period is other than 1 minutes.

In another embodiment of the present invention, a feedback mechanism may be provided where the duty cycle is varied to achieve a desired response, such as a specific transient response time. In this case, the final duty cycle is the parameter that is correlated with the sensor parameter to be estimated. This feedback technique may be extended to other types of control signals, mentioned below, and other characteristics of the signal such as phase, amplitude and frequency may be varied to achieve a desired response.

Alternatively, a sine wave may be used as the control signal discussed above rather than a square wave. Still alternatively, a series of sine waves at different frequencies, or a chirp signal may be used as control signals in one embodiment of the present invention. The measured response of these perturbation signals may then be analyzed using standard spectral analysis techniques. Based on the spectral analysis, metrics may be determined that are correlated with the sensor parameter to be estimated.

In accordance with yet another embodiment, an impulse signal, or a series of impulse signals may be alternatively used as control signals. The measured response of these perturbation signals may be analyzed using known impulse response analysis techniques. For example, the maximum height of the measured response may be used to determine the associated sensor sensitivity. Alternatively, other signal metrics such as the time to reach the maximum height of the measured response, the area under the curve of the measured response, the slope of the measured response may be correlated with the sensor parameter to be estimated.

In still another embodiment, pseudo-random modulation similar to those used in spread-spectrum communication systems may be used as the control signals. The measured response of these perturbation signals may be analyzed using known spread-spectrum analysis techniques. Based on this analysis, metrics may be determined that are correlated with the sensor parameter to be estimated. In addition, the response signal may be demodulated using spread-spectrum techniques to recover the analyte level.

For some of the control signal/response measurement analysis techniques discussed above, the relative phase between the control signal and the measured response may be used to analyze the measured response to the perturbation. For some of the control signal/response measurement analysis techniques discussed above, multiple metrics may be determined. One or more of these metrics may be used to estimate the sensor parameter of interest. For example, in one embodiment, a multidimensional table lookup may be used where one dimension includes the sensor parameter of interest, and the other dimensions may each be associated with a different metric that characterizes the measured response. More specifically, by way of illustration, in the impulse response approach described above, both the maximum height and the time to reach the height of the measured response may be determined. In this case, a three dimensional lookup table may be used.

As discussed above, in one embodiment, a lookup table may be used to correlate a metric associated with the measured response with a sensor parameter of interest (for example, sensitivity). Alternatively, a mathematical function that relates the measured response metric with the sensor parameter may be used. The sensor parameter may then be determined based on the measured response metric as an input. In another aspect, the estimate of the sensor parameter may be determined for many measurements using, for example, the least squares approach.

In addition, within the scope of the present invention, the control signal may be transmitted to the analog interface 201 at predetermined time periods during the life of the sensor. Alternatively, the transmitter processor 204 may be configured to transmit the control signal only during the time periods when sensor calibration is desired or if some other factor, such as a detection of sensitivity instability, determines that sensor calibration is required.

Moreover, in one embodiment, other system parameters in addition to sensitivity may be associated with the measured response from the analog interface 201 in response to the control signal from the transmitter processor 204. These include, but are not limited to, sensor response time, sensor response linearity, sensitivity stability and sensor failure. Accurately estimated sensor response time can be useful for incorporation into algorithms that compensate for errors due to lag in the analyte measurement system. Knowledge of the non-linearity in the sensor response (non-linearity means that the sensitivity is not constant over the entire range to measured response) allows for compensation of errors caused by this non-linearity.

Detection of sensitivity instability (that is, detection when the sensitivity has changed value) may be used to accurately determine the new sensitivity. For example, if instability has been detected by the signal processing component, it can direct the control processing component such as the transmitter unit processor 204 to initiate a control signal that is more appropriate to accurately estimating the sensitivity. Also, detecting a sudden, substantial change in sensitivity may be used to identify that a sensor may have failed.

While the control signal may be used to determine the sensor sensitivity, in one embodiment, the resulting modulation in the measured response may be removed by, for example, one or more signal filters to recover the glucose signal. In one aspect, a standard signal filter may be used to remove the high frequency content of the signal due to modulation by the perturbation control signal, and recover the lower frequency content that represents the analyte level. In another aspect, the modulation may be deconvolved using the control signal, the calculated sensor response and the estimated sensitivity.

Furthermore, there are several approaches to measure a sensor's response to the perturbation signals in order to estimate desired properties or characteristics of the sensor. For example, in one embodiment, the electrical current that flows through the work (and counter) electrode may be measured. Alternatively, the perturbation response in the counter electrode voltage may be alternatively measured. The measured counter voltage response may be analyzed using same or similar techniques as the measured work current response. In another embodiment, both work current and counter voltage responses may be measured and analyzed.

In the manner described above, within the scope of the present invention, there is provided method and system for performing calibration of analyte sensors based on the sensor dynamic behavior and on a substantially real time basis such that sensor calibrations based on blood glucose measurements may be minimized and further to improve the accuracy of the analyte sensor data.

In accordance with the various embodiments of the present invention, the transmitter processor 204 may include a microcontroller, or alternatively, may be implemented with digital logic such as a gate array or similar logic devices. In addition, in one embodiment, the measured response variance as well as the estimated sensor sensitivity determined by the transmitter processor 204 may be transmitted to the receiver unit 104 (FIG. 1) in the analyte monitoring system 100 in addition to the analyte sensor measurements (for example, the work electrode current measurements detected by the sensor unit 101).

In a further aspect, some of the processing may be performed by the receiver unit 104 (FIG. 1) rather than by the transmitter processor 204 such that the transmitter unit 102 may be configured to periodically transmit the measured response variance to the receiver unit 104, and the receiver unit processing and storage unit 307 (FIG. 3) may be configured to perform the sensor sensitivity determination based on the lookup table which may be stored in a memory device (not shown) in the receiver unit 104.

A method of calibrating an analyte sensor in one embodiment includes applying a control signal, detecting a measured response to the control signal, determining a variance in the detected measured response, and estimating a sensor sensitivity based on the variance in the detected measured response.

The level of the control signal may in one embodiment vary in time.

In one aspect, the control signal may include a square wave signal, where the square wave signal may be applied to a poise voltage.

In a further aspect, detecting the measured response may include determining a work electrode current signal.

In still another aspect, the variance may be determined based on comparing the difference between the beginning and end of the half duty cycle of the measured response to the control signal.

Moreover, estimating the sensor sensitivity may include retrieving a predetermined sensor sensitivity corresponding to the determined variance in the detected measured response.

The method may also include determining a validity of the estimated sensor sensitivity.

In addition, the method may also include determining analyte level based on the estimated sensor sensitivity.

The sensor in one embodiment may include an analyte sensor.

An analyte sensor calibration device in accordance with another embodiment includes a processor configured to apply a control signal, detect a measured response to the control signal, determine a variance in the detected measured response, and estimate a sensor sensitivity based on the variance in the detected measured response.

The processor may be configured to vary the level of the control signal with time.

In another aspect, the processor may be configured to apply a square wave signal to a poise voltage.

The processor in a further aspect may be configured to determine a work electrode current signal of an analyte sensor operatively coupled to the processor.

Moreover, the processor may be configured to determine the variance based on comparing the difference between the beginning and end of the half duty cycle of the measured response to the control signal.

In addition, the processor in a further aspect may be configured to retrieve a predetermined sensor sensitivity corresponding to the determined variance in the detected measured response.

The processor may be operatively coupled to a data receiver unit configured to determine determining a validity of the estimated sensor sensitivity, where the data receiver unit may be configured to determine an analyte level based on the estimated sensor sensitivity.

The various processes described above including the processes performed by the transmitter processor 204 in the software application execution environment in the transmitter unit 102 including the processes and routines described in conjunction with FIGS. 4-6 and 9, may be embodied as computer programs developed using an object oriented language that allows the modeling of complex systems with modular objects to create abstractions that are representative of real world, physical objects and their interrelationships. The software required to carry out the inventive process, which may be stored in the memory (not shown) of the transmitter unit 102 may be developed by a person of ordinary skill in the art and may include one or more computer program products.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method of calibrating an analyte sensor, comprising:
   applying a control signal to the analyte sensor;
   detecting a measured response to the control signal;
   determining a variance in the detected measured response; and
   estimating, with a processor, a sensor sensitivity based on the variance in the detected measured response.

2. The method of claim 1 wherein the level of the control signal varies in time.

3. The method of claim 1 wherein the control signal includes a square wave signal.

4. The method of claim 3 wherein the square wave signal is applied to a poise voltage.

5. The method of claim 1 wherein detecting the measured response includes determining a work electrode current signal.

6. The method of claim 1 wherein the variance is determined based on comparing the difference between the beginning and end of the half duty cycle of the measured response to the control signal.

7. The method of claim 1 wherein estimating the sensor sensitivity includes retrieving a predetermined sensor sensitivity corresponding to the determined variance in the detected measured response.

8. The method of claim 1 further including determining a validity of the estimated sensor sensitivity.

9. The method of claim 1 further including determining analyte level based on the estimated sensor sensitivity.

10. The method of claim 1 wherein the sensor includes an analyte sensor.

11. An analyte sensor device, comprising:
    a processor configured to apply a control signal to the analyte sensor, detect a measured response to the control signal, determine a variance in the detected measured response, and estimate a sensor sensitivity based on the variance in the detected measured response.

12. The device of claim 11 wherein the processor is configured to vary the level of the control signal with time.

13. The device of claim 11 wherein the control signal includes a square wave signal.

14. The device of claim 13 wherein the processor is configured to apply the square wave signal to a poise voltage.

15. The device of claim 11 wherein the processor is configured to determine a work electrode current signal of an analyte sensor operatively coupled to the processor.

16. The device of claim 11 wherein the processor is configured to determine the variance based on comparing the difference between the beginning and end of the half duty cycle of the measured response to the control signal.

17. The device of claim 11 wherein the processor is configured to retrieve a predetermined sensor sensitivity corresponding to the determined variance in the detected measured response.

18. The device of claim 11 wherein the processor is operatively coupled to a data receiver unit configured to determine determining a validity of the estimated sensor sensitivity.

19. The device of claim 18 wherein the data receiver unit is configured to determine an analyte level based on the estimated sensor sensitivity.

20. The device of claim 11 wherein the processor is operatively coupled to an analyte sensor.

* * * * *

UNITED STATES PATENT AND TRADEMARK OFFICE
CERTIFICATE OF CORRECTION

PATENT NO. : 7,653,425 B2
APPLICATION NO. : 11/463582
DATED : January 26, 2010
INVENTOR(S) : Hayter et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 269 days.

Signed and Sealed this

Twenty-third Day of November, 2010

David J. Kappos
*Director of the United States Patent and Trademark Office*